United States Patent
Chetboun

(12) 
(10) Patent No.: US 9,220,275 B2
(45) Date of Patent: Dec. 29, 2015

(54) METHOD FOR ACARICIDAL AND MICROBICIDAL TREATMENT OF TEXTILE MATERIALS

(75) Inventor: Nathalie Chetboun, Marseilles (FR)

(73) Assignee: YEREB LAB LTD., Nicosia (CY)

( * ) Notice: Subject to any disclaimer, the term of this patent is extended or adjusted under 35 U.S.C. 154(b) by 2908 days.

(21) Appl. No.: 10/480,808

(22) PCT Filed: Jun. 19, 2002

(86) PCT No.: PCT/FR02/02108
§ 371 (c)(1),
(2), (4) Date: Jun. 7, 2004

(87) PCT Pub. No.: WO03/002807
PCT Pub. Date: Jan. 9, 2003

(65) Prior Publication Data
US 2010/0092529 A1    Apr. 15, 2010

(30) Foreign Application Priority Data
Jun. 22, 2001 (FR) ...................................... 01/08282

(51) Int. Cl.
```
A61K 9/00      (2006.01)
A61K 36/58     (2006.01)
B05D 3/00      (2006.01)
A01N 65/26     (2009.01)
A01N 65/00     (2009.01)
D06M 13/00     (2006.01)
D06M 16/00     (2006.01)
D06M 19/00     (2006.01)
D06M 23/12     (2006.01)
```

(52) U.S. Cl.
CPC ................ *A01N 65/26* (2013.01); *A01N 65/00* (2013.01); *D06M 13/005* (2013.01); *D06M 16/00* (2013.01); *D06M 19/00* (2013.01); *D06M 23/12* (2013.01)

(58) Field of Classification Search
CPC ....... A01N 65/00; A01N 65/26; A01N 25/34; A01N 25/28; A01N 2300/00; D06M 13/005; D06M 16/00; D06M 19/00; D06M 23/12
See application file for complete search history.

(56) References Cited

U.S. PATENT DOCUMENTS

| | | | | |
|---|---|---|---|---|
| 4,464,431 A | * | 8/1984 | Hisaki et al. ................... | 442/101 |
| 4,882,220 A | * | 11/1989 | Ono et al. ......................... | 442/96 |
| 5,232,769 A | * | 8/1993 | Yamato et al. .................. | 442/123 |
| 5,292,533 A | * | 3/1994 | McMahon et al. ............. | 424/408 |
| 5,518,764 A | * | 5/1996 | Traubel et al. ................. | 427/209 |
| 5,788,975 A | * | 8/1998 | Laversanne et al. ........... | 424/417 |
| 6,060,075 A | * | 5/2000 | Rao et al. ....................... | 424/405 |

FOREIGN PATENT DOCUMENTS

| | | | |
|---|---|---|---|
| DE | 19532447 | | 3/1997 |
| DE | 19654689 | * | 7/1998 |
| EP | 0494067 | | 7/1992 |
| EP | 0863248 | | 9/1999 |
| GB | 1401143 | | 7/1975 |
| WO | WO 00/05964 | * | 2/2000 |

OTHER PUBLICATIONS

Aminabhavi et al., Polymeric Microspheres/granules Containing a Liquid Pesticide [*Azadirachta indica* (neem)] for Soil Applications, Polymer News (1999). 24(6), 211-213.*
XP-002247033, Abstract JP 02 200602 A, Aug. 88, 1990.
XP-002247034, Abstract JP 04 100980 A, Apr. 2, 1992.

* cited by examiner

*Primary Examiner* — Anoop Singh
*Assistant Examiner* — Doan Phan
(74) *Attorney, Agent, or Firm* — Ladas & Parry LLP

(57) ABSTRACT

The present invention concerns a method of agaricidal and microbicidal treatment of textile materials, a Neem oil microcapsule composition specifically for said treatment and a bioactive textile material obtained. More particularly, the present invention concerns the industrial and commercial areas of the treatment of fabrics and like products and is of particular application to textile materials produced from natural fibers such as cotton, feathers or down, or synthetic fibers such as polyester, nylon, acrylic or the like, or mixed fibers such as polyester-cotton. The present invention concerns a method of agaricidal and microbicidal treatment of a textile material, in which microcapsules containing Neem oil are fixed on said textile material.

9 Claims, No Drawings

METHOD FOR ACARICIDAL AND MICROBICIDAL TREATMENT OF TEXTILE MATERIALS

The present invention relates to a method of acaricidal and microbicidal treatment of textile materials, to a Neem oil microcapsule composition specifically for said treatment, and to a bioactive textile material obtained.

More particularly, the present invention relates to the industrial and commercial fields of treating fabrics and like products and is of particular application to textile materials formed from natural fibers such as cotton, feathers, down, or synthetic fibers such as polyester, nylon, acrylic or the like, or mixed fibers such as polycotton.

BACKGROUND OF THE INVENTION

Mites are small arachnids that are known to flourish in dwellings and to proliferate in the constituent textile materials of bed linen, carpets and upholstery, for example, causing serious problems to man, especially respiratory problems characterized by allergies or asthma, the remedies for which must be taken continuously.

Current acaricidal compounds are usually of the perithrenoid type.

Said compounds have a certain level of toxicity and have deleterious ecological effects since they are not biodegradable.

OBJECTS AND SUMMARY OF THE INVENTION

A first aim of the present invention is to provide a method of acaricidal treatment of textile materials, which is non toxic and which is acceptable from an ecological viewpoint.

The method of the present invention also proposes a novel treatment for the textile materials themselves by endowing them with bioactive, acaricidal/mite-inhibiting and microbicidal properties which are effective over time, in particular over a fairly long period, and which can resist several washes, in particular machine washes, without losing their efficacy.

A product is known from European patent EP-A-0 436 257 which is an insecticide in the field of wood, agriculture, and animal welfare for controlling pest insects such as mosquitoes, tics, flies and fleas, as well as certain bacterial species. It is a natural vegetable oil extracted from Neem seeds. Neem (*Azadirachta indica*) is a tree belonging to the mahogany family which can reach 15 meters in height and is widespread in tropical and subtropical regions, more particularly in India, Africa, Indonesia, and South America.

Neem oil can be extracted by cold pressing Neem seeds or by solvent extraction as described in EP-A-0 494 067 and International patent application WO-A-97/25867.

Neem oil is a product which is biodegradable and neither toxic nor allergenic.

Neem oil has never been proposed for the acaricidal treatment of textile materials, as it has a large number of disadvantages, including:

1/ a repugnant garlic odor;
2/ rapid oxidation, producing a beige-brown color;
3/ degradation of the active compounds under ultraviolet (UV) light and at a temperature higher than 65° C.; and
4/ degradation of the active compounds in contact with water.

The above disadvantages constitute obstacles which have dissuaded the skilled person from using Neem oil in fabrics intended for household use.

In particular, the physico-chemical properties of Neem oil are incompatible with resistance to the machine washing and drying which is unavoidable in the industrial utilization of fabrics and bed linen.

Microencapsulating liquid or solid substances, imprisoning such substances in microcapsules with polymeric walls, is known. Protected by their microcapsules, the active agents are only released when the microcapsules burst when brought into contact with certain media or are subjected to certain conditions which cause them to split or rupture.

Treating textile materials on an industrial scale with different finishes to endow them with different properties such as flame-retardant or stain-repellant properties, the application of fillers or even glazing, involves padding treatments followed by a drying step at temperatures of over 120° C. to obtain rapid drying.

Such drying temperatures are incompatible with maintaining the active properties of Neem oil.

The inventor has discovered that it is possible to carry out an acaricidal and microbicidal treatment on textile materials which satisfies the aims of the present invention and overcomes the various disadvantages of Neem oil described above, by treating said textile materials with Neem oil in the microencapsulated form, i.e., in the form of micro-droplets of Neem oil enveloped in a polymeric wall.

Thus microencapsulated, the Neem oil endows said textile materials with acaricidal and microbicidal properties, with the active substances in the Neem oil being released by rupture of the microcapsules following a simple mechanical process of rubbing said textile material into which they have been incorporated.

Said microcapsules act as a vehicle for fixing the Neem oil onto the textile material, improving the bioavailability of its active principles, masking the disagreeable odors of certain of its compounds, and increasing the lifetime of said substances.

The active molecules act in the core of the fibers, blocking the growth and reproduction of the mite pests via enzymatic systems.

The inventor has discovered that it is possible to produce Neem oil microcapsules that preserve the properties of the active substances in the Neem oil over time even after washing and high temperature drying treatments. Further, the microcapsules are stable over time and the acaricidal and microbicidal characteristics of said textile material treated with said microcapsules are maintained even after several washes.

Thus, microencapsulation can solve the problems of many agaricides as regards application to textile materials and as regards long-term, effective release of active substances from textile materials.

In particular in microcapsules, the color and odor of the Neem oil are overcome, even more so when the Neem oil is mixed with other agents, allowing a desired odor to be obtained.

Thus, the present invention provides a method of acaricidal and microbicidal treatment of a textile material in which microcapsules containing Neem oil are fixed to a textile material.

Advantageously, to obtain an effective treatment over time, a sufficient quantity of microcapsules is fixed to said textile material to obtain a concentration by weight of 0.1% to 3% of Neem oil in said textile material.

Of the 200 active compounds in Neem oil, azadirachtin A, nimbin, and salanim are, in accordance with the invention, the principal compounds with an acaricidal action, acting against the development and reproduction of mites.

Preferably, a specifically reformulated Neem oil is employed to obtain a concentration enriched in active molecules, containing the following proportions by weight:

1% to 30% of nimbin, preferably 1% to 25%;
1% to 30% of salanim, preferably 2% to 30%;
0.15% to 20% of azadirachtin A, preferably 1% to 20%.

In one implementation, the microcapsules represent a good compromise between wash resistance, good attachment to textile materials, ability to burst or rupture by simple rubbing, and finally treatment efficacy; said microcapsules are constituted by a polymer selected from aminoplast resins, namely resins resulting from polycondensing an aldehyde with an amine or an amide, more particularly a urea-formol type polymer.

Preferably again, said microcapsules are coated with a film of polymeric binders encouraging fixing of said microcapsules to said textile material and increasing the resistance of said microcapsules and the active molecules contained in the Neem oil to degradation; preferably again, said polymer binder provides softening properties.

More particularly advantageously, in the method of the invention, said textile material is treated by soaking or spraying with a composition of said Neem oil microcapsules.

Many microencapsulation means are known to the skilled person.

However, because of the risks of degrading the active substances in Neem oil, a microencapsulation method is employed that does not involve temperatures of more than 65° C. More particularly, microencapsulation is carried out by in situ polymerization of said constituent polymers of the wall in a Neem oil formulation, said in situ polycondensation polymerization being carried out at a temperature of less than 65° C.

This in situ polymerization method is particularly advantageous as it involves strong bonds between the molecules of the polymers constituting the wall, which can preserve the properties of the acaricidal substances long-term even after machine washing, and which can release said substances by rupture of the wall by rubbing.

In a preferred implementation, in the method of the invention said textile material is initially soaked with said Neem oil microcapsules composition followed, after using said treated textile material, by spraying or soaking said textile material again with a said Neem oil microcapsule composition, preferably at least every five washes of said textile material.

Preferably, said Neem oil microcapsule composition comprises a dispersion of microcapsules mixed with dispersions of polymeric binders, said binders being selected to encourage attachment of said microcapsules to said textile material, and to increase the resistance of said microcapsules and said active molecules contained in the Neem oil to high temperature degradation, preferably at a temperature of more than 65° C., more preferably at a temperature of more than 150° C.

This type of soaking treatment involves industrial drying processes carried out at temperatures of the order of 150° C. which, according to the present invention, do not denature the active substances in the Neem oil, nor the microcapsules.

The method of the invention thus consists of impregnating the textile material to be treated with a finish applied either by spraying or soaking in a bath, to incorporate into said fabric a concentration of Neem oil of 0.1% to 3% by weight.

In a preferred implementation of the method of the invention, said binders are selected from polyurethane and polysiloxane binders.

The polyurethane type binder encourages attachment of the microcapsules to the fabric and increases the resistance to machine washing, and the polysiloxane type binder also contributes to increasing the high temperature degradation resistance, this protective effect being paired with a softening effect.

The use of a silicone polysiloxane-based binder provides softening properties; adding microcapsules to a fabric would otherwise roughen the fabric.

More particularly, and especially when the microcapsules are produced with aminoplast resin walls, more particularly urea-formol in type, said textile material is treated by soaking in an aqueous composition of Neem oil microcapsules containing the following concentrations by weight:

at least 0.5%, preferably at least 3%. of said Neem oil microcapsules;
at least 1.5%, preferably at least 10%, of polyurethane binders;
at least 0.3%, preferably at least 2%, of polysiloxane binder.

Still more particularly, said Neem oil microcapsules composition for acaricidal and microbicidal treatment of textile materials contains an effective quantity of Neem oil microcapsules, as defined above, preferably as a mixture with polymeric binders as defined above.

The use of said polymeric binders endows said treatment with good washing resistance, i.e., good attachment of the microcapsules to the fabric, in particular for up to five consecutive washes, and good microcapsule strength; the microcapsules can achieve a service life of three years and achieve long-term resistance to degradation, as well as protect against denaturing of the active substances they contain, up to temperatures of at least 150° C.

The present invention also concerns a bioactive textile material obtained by a treatment method in accordance with the invention and, more particularly, a bioactive textile material which comprises Neem oil microcapsules, preferably with a Neem oil content of at least 0.1% by weight, more preferably at least 0.3%, said microcapsules preferably being coated with a film of polymeric binders encouraging fixing of said microcapsules in said textile material and increasing the degradation resistance of said microcapsules and the active molecules contained in the Neem oil; more preferably, said polymeric binder endows the microcapsules with softening properties.

Still more particularly, a bioactive textile material in accordance with the invention comprises Neem oil microcapsules produced from an aminoplast polymer and comprising a coating of at least one polymeric binder comprising at least a polyurethane and/or polysiloxane.

Laboratory experiments carried out on the most resistant and virulent dust mites as regards allergies, namely *Dermaphagoïde pteronissimus*, exhibited 90% mortality after three weeks (one reproductive cycle) and 100% mortality after four weeks.

It was also shown that the treated textiles are provided with an ability to transfer the acaricidal/mite-inhibiting properties by diffusion of the released active principles onto untreated textile materials in contact with a treated textile.

From a toxicological viewpoint, the tests carried out have shown that toxicologically, this finish is non toxic and inoffensive as regards mammals, fishes, birds, and bees. Furthermore, it is hypoallergenic, even after a long period of contact with the skin.

It is possible to couple the Neem oil in the microcapsules with a further natural vegetable oil with similar physico-chemical properties to endow the bioactive materials with complementary properties; for example, Saint-John's wort oil can be coupled with the Neem oil in a ratio of 3%. This produces a material that is also bactericidal/bacteria-inhibiting.

It is also possible to add perfumed or deodorizing essences to the microcapsules, selected as a function of the use of the product to be treated.

The treated textile materials can be used in areas such as bed linen (manufacture of eiderdowns, duvets, pillows, sheets, pillowcases, etc.), and in certain textiles such as curtains or carpets. They can also be used in the manufacture of storage items such as furniture covers, garment covers, duvet covers, etc.

The arrangement and combination of the various constituent elements of the invention maximizes its advantages, which have not until now been produced by similar methods.

DETAILED DESCRIPTION OF THE EXAMPLES

Other characteristics and advantages of the present invention will become apparent from the following examples.

Example 1

Preparation of a Neem Oil Microcapsule Composition

We used a Neem oil known as "Plasma Neem Oil" from Plasma Power (India), said oil deriving from India and being obtained by traditional extraction from seeds. This oil has the following active components in the following proportions by weight:
nimbin: 1%;
salanim 2%;
azadirachtin A: 0.15%.

Microcapsules were also produced with Neem oil supplied by FLAVEX (Germany), obtained by extraction with an organic solvent.

Microencapsulation was carried out using the in situ polycondensation polymerization method known to the skilled person.

The polymer used to produce the microcapsules was a urea-formol resin.

Particles 1 to 5 microns in size were obtained; more precisely, the majority of microcapsules were of the order of 2 microns.

At the end of the encapsulation process, a dispersion of microcapsules comprising 30% Neem oil was obtained.

For the purposes of improving fixing of the microcapsules in the fabrics, a treatment was carried out in a basic medium at a pH of 8-9 by mixing the white colored dispersion of microcapsules obtained at the end of the microencapsulation process with an aqueous dispersion of a polyurethane binder (ROTTA-COATING 96-730 from ROTTA (Germany)). The binder tended to form a film around the microcapsules.

The weight ratio (microcapsule dispersion/polyurethane binder dispersion) employed was 15/50.

To this dispersion of microcapsules in the polyurethane binder, we then added a silicone micro-emulsion, based on slightly cationic ROMA-SILIKON polysiloxane polymers from ROTTA, which also contributed to creating a protective film around the microcapsules.

A slightly viscous aqueous white dispersion was obtained.

Example 2

Acaricidal Fabric Treatment

Several types of the fabrics generally used in the bed linen industry were treated, namely 100% cotton fabrics with a GSM of 100 to 130 grams/m$^2$, mixed fabrics, 100 gram/m$^2$ polyester/cotton, gray (crude fabric), prewashed, desized or finished with flame retardant, stain repellant finishes such as Teflon, fillers, or glazed.

We carried out a treatment by soaking microcapsules obtained in accordance with Example 1 comprising, per liter of bath:
30 grams of microcapsules;
100 grams of polyurethane binder;
20 grams of silicone.

For the fabrics used, the degree of absorption was 70%, namely 70 grams of aqueous composition absorbed per 100 grams of initial dry fabric.

The aqueous soaking composition employed produced a weight concentration of 2 grams of capsules per 100 grams of fabric, namely a concentration of Neem oil deposited on the fabric of 0.6% (0.6 grams per 100 grams of fabric).

The fabric was dried at 150° C. for 60 seconds.

The microcapsules resisted a pressure of 3 bars on stenters.

Clearly, the composition of the bath and the concentration of the different constituents of the bath are adapted as a function of the degree of absorption of the fabrics, taking into account the concentrations by weight of Neem oil to be deposited on the fabric.

Regarding the treatment of glazed fabric, to avoid losing the glaze, a spray treatment was carried out rather than soaking. 10 grams of a formulation of an aqueous composition with the same composition as the soaking bath described above, in an amount of 10 grams of formulation per 100 grams of fabric, was sprayed to obtain a weight ratio of 0.6% of Neem oil on the textile material after drying at 150° C. for 30 seconds.

Example 3

Measurement of the Effectiveness of Treatments Intended to Combat Dust Mites

1/ Principle:

The impact of the fabric treatment obtained using the operating procedure of Example 2 but with a weight content of only 0.3% of Neem oil on the fabric was evaluated against the evolution of a dust mite population (*Dermatophagoïdes Pteronyssinus*) by comparison with a population not subjected to the product.

This evaluation was carried out by depositing mites onto supports impregnated or not impregnated with the active principles.

2/ Original Mite Rearing:

The mites used (*Dermatophagoïdes Pteronyssinus*) derived from a laboratory strain reared on a substrate composed of a 50/50 (weight/weight) mixture of wheatgerm and beer yeast in flakes calibrated by sieving to fragments less than 1 mm in size. The temperature was in the range 23° C. to 25° C. and the relative humidity was maintained at 75% by bringing it into the presence of a saturated ammonia solution ($[NH_4+_2SO_4]$); the strain was kept in the dark. The strain was supplied by the Laboratoire des Insectes et Acariens des Denrées de l'Institut National de Recherches Agronomiques de Bordeaux (I. N. R. A.).

3/ Experimental Method:

The experimental unit was constituted by a 5 cm diameter chamber that was sealed to mites but allowed aeration via a filter paper and which contained:
0.05 g of nutrient substrate/dust intended to ensure that the mites were fed;

a piece of PVC covering the bottom of this unit, coated with treated fabric;

100 to 200 mites deposited on the fabrics.

The mites intended for the tests had been sorted in advance to retain the most active mites.

Four repetitions were carried out by a laboratory technician, including the CONTROL batches constituted by the same device but with an untreated support.

The experimental units were isolated by the technician in polypropylene tanks, maintaining the relative humidity and keeping the conditions optimal for identical development under the conditions mentioned in paragraph 2 above.

4/ Controls and Results:

Mortality was determined by counting under a binocular magnifying glass using a hand counter and the method developed and tested by I. N. R. A., Bordeaux.

Mortality was monitored at a fortnight, 4 weeks and 6 weeks after depositing the mites on the treated cotton supports or controls of standard untreated cotton.

The measurements were made by the same operative and the criteria for mortality were as follows:

mites incapable of moving were classified as dead;
mites capable of moving were classified as alive.

The textile support was rubbed using a spatula once a week for 30 seconds under identical conditions.

The results are shown in Table 1 below.

The counts show the % mortality;

Under these test conditions, with the samples, mites and methodology used: the mortalities obtained with the untreated batches were sufficiently low to validate the test.

The sample controlled the mite population perfectly over a period of two development cycles (6 weeks).

Example 3. We observed an identical efficiency for the fabric after 5 washes compared with the unwashed control, which meant that the weight content of 0.3% by weight of Neem oil could be further reduced while maintaining the activity with the Neem oil used.

What is claimed is:

1. A method of treatment of a textile material conferring acaricidal properties to the material, the method comprising:
    contacting said textile material with a dispersion comprising:
    a binder consisting essentially of a polyurethane binder and a polysiloxane binder; and
    a composition containing Neem oil encapsulated in microcapsules comprising an aminoplast resin polymer,
    wherein said microcapsules release neem oil only by rupture of the microcapsules following a simple mechanical process of rubbing said textile material while masking the neem oil odor;
    wherein said dispersion comprises, by weight:
      at least 0.5% of said Neem oil microcapsules;
      at least 1.5% of said polyurethane binder;
      at least 0.3% of said polysiloxane binder;
    wherein the microcapsules have a size of 1 to 5 microns;
    whereby the microcapsules are coated with a film of the binder; and then
    fixing said microcapsules onto said textile material;
    wherein said microcapsules are fixed onto said textile material such that a concentration of 0.1% to 3% by weight of Neem oil is obtained in said textile material;
    wherein said binder encourages attachment of said microcapsules to said textile material, and increases resistance of said microcapsules to temperature degradation at a temperature of at least 150° C., such that there is a loss of

TABLE 1

| | | MORTALITY | | | POPULATION REDUCTION | | | |
| | | After a fortnight | | | After 4 weeks | | After 6 weeks | |
| Treated textile | Repetition | D | A | % M | A | % reduction | A | % reduction |
| | 1 | 76 | 32 | 70.4 | 0 | 100 | 0 | 100 |
| | 2 | 80 | 28 | 74.1 | 0 | 100 | 0 | 100 |
| | 3 | 61 | 36 | 62.9 | 0 | 100 | 0 | 100 |
| | 4 | 89 | 20 | 81.7 | 0 | 100 | 0 | 100 |
| | Av | | 29 | 72.2 | 0 | 100 | 0 | 100 |
| | Std dev | | | 1.9 | | | | 0 |
| Control | 1 | 8 | 105 | 7.1 | 469 | — | 1320 | — |
| | 2 | 5 | 96 | 5.0 | 481 | — | 1151 | — |
| | 3 | 7 | 115 | 5.7 | 379 | — | 1274 | — |
| | 4 | 5 | 85 | 5.6 | 406 | — | 1056 | — |
| | Av | | 100.25 | 5.8 | 433.8 | — | 1200.3 | — |
| | Std dev | | | 1.1 | 49.1 | — | 119.7 | — |

D = Dead
A = Alive
% M = % mortality

Example 4

Microcapsule Strength and Maintaining Activity After Washing

Five successive machine washes were carried out on the bioactive textiles and the resistance of the microcapsules and persistence of the acaricidal effectiveness was monitored. The resistance of the microcapsules was observed using a scanning electron microscope. A loss of only 30% of the microcapsules was observed compared with the control. The efficiency was measured using the protocol described in no more than 30% of the microcapsules after five washings of textiles treated with the dispersion.

2. The method according to claim 1, wherein the Neem oil is enriched in active molecules such that the Neem oil contains, by weight:
    1% to 30% of nimbin;
    1% to 30% of salanim; and
    0.15% to 20% of azadirachtin A.

3. The method according to claim 1, wherein said textile material is contacted by soaking or spraying with said dispersion.

4. The method according to claim 3, wherein an initial soaking or spraying of said textile material is carried out with said dispersion, and after using said textile material, by again soaking or spraying with said dispersion.

5. The method according to claim 1, wherein the weight ratio of polyurethane binder to microcapsules in the dispersion is not higher than 50:15.

6. The method according to claim 1, wherein the dispersion is an aqueous dispersion.

7. The method according to claim 1, wherein there is a loss of no more than 30% of the microcapsules after five washings at a temperature of more than 150° C.

8. The method according to claim 1, wherein a weight ratio of polyurethane binder:polysiloxane binder is 5:1.

9. The method according to claim 1, wherein a majority of the microcapsules have a size in the order of 2 microns.

* * * * *